United States Patent
Benner et al.

(10) Patent No.: US 10,059,735 B1
(45) Date of Patent: Aug. 28, 2018

(54) NUCLEOSIDE HETEROCYCLE THAT BINDS TO BOTH THYMIDINE AND CYTIDINE

(71) Applicants: Steven A Benner, Gainesville, FL (US); Hyo-Joong Kim, Gainesville, FL (US)

(72) Inventors: Steven A Benner, Gainesville, FL (US); Hyo-Joong Kim, Gainesville, FL (US)

( * ) Notice: Subject to any disclaimer, the term of this patent is extended or adjusted under 35 U.S.C. 154(b) by 0 days.

(21) Appl. No.: 15/377,236

(22) Filed: Dec. 13, 2016

Related U.S. Application Data

(60) Provisional application No. 62/267,382, filed on Dec. 15, 2015.

(51) Int. Cl.
| | |
|---|---|
| *C07H 19/22* | (2006.01) |
| *C07H 19/24* | (2006.01) |
| *C07H 21/04* | (2006.01) |
| C07H 21/02 | (2006.01) |
| C07H 19/04 | (2006.01) |
| C07H 19/23 | (2006.01) |

(52) U.S. Cl.
CPC .............. *C07H 19/24* (2013.01); *C07H 21/04* (2013.01); *C07H 19/04* (2013.01); *C07H 19/23* (2013.01); *C07H 21/02* (2013.01)

(58) Field of Classification Search
None
See application file for complete search history.

(56) References Cited

PUBLICATIONS

Araujo et al. Collection Symposium Series (2002), 5 (Chemistry of Nucleic Acid Components), 328-331.*

* cited by examiner

*Primary Examiner* — Patrick T Lewis

(57) ABSTRACT

This application discloses nucleoside analogs that when incorporated into a oligonucleotide, forms a nucleobase pair with either thymidine or cytidine that are present in a complementary strand at the paired position. These analogs are called "purine biversals". Such compounds and their associated processes have utility in processes that detect complementary oligonucleotides, in particular oligonucleotides from natural sources and in complex biological mixtures, where the sequence of the complementary oligonucleotide being detected is not known precisely. The invention also includes compositions of matter that are oligonucleotides that contain purine biversals of the instant invention, and duplexes of said oligonucleotides.

5 Claims, 9 Drawing Sheets complements T in a Watson-Crick geometry

*tautomerism* complements C in a Watson-Crick geometry

NUCLEOSIDE HETEROCYCLE THAT BINDS TO BOTH THYMIDINE AND CYTIDINE

STATEMENT OF RIGHTS TO INVENTIONS MADE UNDER FEDERALLY-SPONSORED RESEARCH

This invention was made with government support under W81XWH-15-C-0007 awarded by USA Medical Research and Material Command, 1R41AI116445-01 awarded by the National Institute of Allergy and Infectious Diseases, and 1R43GM114967-01 awarded by the National Institute of General Medical Sciences. The government has certain rights in the invention.

CROSS REFERENCE TO RELATED APPLICATIONS

None

THE NAMES OF PARTIES TO A JOINT RESEARCH AGREEMENT

Not applicable

INCORPORATION BY REFERENCE OF MATERIAL SUBMITTED ON A COMPACT DISK

None

BACKGROUND OF THE INVENTION

1. Field of the Invention

This invention relates to the field of nucleic acid chemistry, more specifically to nucleoside and nucleotide analogues, and most specifically to such analogs that, when incorporated into a DNA strand, are capable of forming Watson-Crick pairs in a Watson-Crick geometry with nucleotides on a complementary strand to form a double helix. The invention covers nucleoside analogues that can form such Watson-Crick pairs with more than one standard nucleotide, specifically analogues that pair which natural thymine and natural cytosine in that complementary strand.

Background

A wide variety of analytical procedures, including those used in human diagnostics, use DNA and/or RNA (collectively xNA) molecules as probes and primers in aqueous and buffered aqueous solution, to bind to substantially complementary oligonucleotides in a biological sample via Watson-Crick pairing. Here, "substantially complementary" means that most of the bases in a probe or primer sequence are complementary and the Watson-Crick sense to most of the bases in the sequence to which it hybridizes. The number of mismatches is therefore insufficient to cause the desired hybrid duplex to fall apart, or "melt", the temperature where utility is found. For example, this binding is often done to detect the DNA or RNA of infectious agents, such as herpes, HIV, or hepatitis viruses. When used for this purpose, biological samples can be complex, such as blood, and can contain many other nucleic acids.

This binding may then be used (without limitation) to capture a target oligonucleotide, for example, or as a primer to initiate the synthesis of a complement of the target oligonucleotide or, with additional primers, a process to amplify the target oligonucleotide sequence so that it can be more easily manipulated and detected. Amplification processes include the polymerase chain reaction (PCR), but also many isothermal application methods.

Unfortunately, in a real diagnostics setting, the target sequence may not be precisely known at all of the sites being complemented by a primer or probe oligonucleotide. This is especially the case with certain RNA viral sequences, which undergo rapid mutation and evolution, often in response to environmental selective pressures. However, viral sequences (and DNA and RNA sequences more generally) also divergently evolve without selective pressure, a process known as "neutral drift". This leads to nucleotide replacement at "silent sites", sites in the gene where changing a nucleotide does not change the sequence of an encoded proteins.

As an example, an analysis of the divergent evolution of the HIV viral genome sequence shows patterns of nucleotide replacement that are attributable to the low fidelity of HIV reverse transcriptase, and the relatively strong selection pressure that operates on the amino acid sequences of the encoded proteins in HIV. Nearly any nucleotide substitution that changes the encoded amino acid is selected against, absent purifying selection pressure. However, variation at the third site of a triplet codon is often silent, and is observed to occur frequently as no purifying selection prevents it from accumulating in a population. From the structure the genetic code, transitions (converting a pyrimidine to another pyrimidine, or converting a purine into another purine) are more likely to be silent than transversions, which interconvert purines and pyrimidines. Therefore, transitions are encountered more frequently. Further, simply due to the mechanism by which mutations arise, transitions are more frequent than transversions.

For such targets that are suffering sequence divergence, those attempting to create useful tools to detect target oligonucleotides need not know exactly what sequence to make as its complement. One common solution in the art manages the sequence ambiguity by simply introducing into the biological sample many different primers and probes having different sequences, sequences that differ at sites in the target oligonucleotide that may hold uncertainty. This solution is satisfactory when the number of uncertain sites is small. However, as the number of uncertain sites becomes large, it becomes impossible to make a large enough number of oligonucleotide probes to cover all potential ambiguities in the target being sought.

A second solution known in the art involves the use of nucleoside analogues known as "universal bases". An ideal universal base pairs with all four of the natural nucleobases with approximately equal affinity. In principle, universal nucleoside analogues can be placed at sites and the primer or probe oligonucleotide intended to Watson-Crick pair with the ambiguous site. Unfortunately, no known heterocyclic system has this ideality. For example, artisans generally use species such as xanthosine as a universal base. However, xanthosine does not perform well as a universal base. Further, the use of xanthosine to hybridized to ambiguous sites does not take advantage of the fact that transitions are more frequent than transversions, creating potential binding diversity in the introduced oligonucleotide far in excess of that normally desired.

A calculation explains why a biversal is preferred over a universal base. A universal nucleobase binds to all four standard nucleotides. If a primer oligonucleotide contains multiple universal nucleobases, it may bind to many places in a complex biological sample, including to segments within (for example) a patient's genomic DNA. If the oligonucleotide is then used as a probe or as a primer in PCR, this off target binding will consume resources that prevent sensitive amplification of the target sequences, and lead to both false negatives and false positives.

2. Description of the Related Art

The instant invention relies on the concept of "biversality", as opposed to universality. Here, two nucleotide analogues are desired, a pyrimidine biversal that pairs with both adenine and guanine, and a purine biversal that pairs with both cytosine and thymine. These can be used separately or together to cover sites whose nucleotide occupancy is unknown in the target oligonucleotide, but where transitions have occurred.

Several biversals are known in the art that serve as a pyrimidine biversal [Lin, P. K., Brown, D. M. (1989) Synthesis and duplex stability of oligonucleotides containing cytosine-thymine analogues. *Nucl. Acids Res.* 17, 10373-10383], in particular, a bicyclic pyrimidine analog (FIG. 1 left) was developed several decades ago by Brown and his coworkers. This heterocycle has two tautomeric forms, one that pairs and a Watson-Crick sense with guanine, the other that pairs with adenine. This equilibrium contains both because of the special features of the R—O—N═C system [Anand, N. N., Brown, D. M., Salisbury, S. A. (1987) The stability of oligodeoxyribonucleotides duplexes containing degenerate bases. *Nucl. Acids Res.* 15, 8167-8176]

Brown et al. attempted as well to create a purine biversal [Brown, D. M., Lin, P. K. T. (1991) Synthesis and duplex stability of oligonucleotides containing adenine-guanine analogs. *Carbohydrate Res.* 216, 129-139]. Here, they attempted to exploit again the special features of the R—O—N═C system by placing a Me-O substituent on the exocyclic nitrogen of diaminopurine (FIG. 1 right). Unfortunately, this substituent can exist in both the cis and trans conformation; in the trans confirmation, it blocks Watson-Crick pairing, which is disadvantageous for its utility.

BRIEF SUMMARY OF THE INVENTION

The instant invention reports a tricyclic nucleobase analog (FIG. 2) that can pair with a Watson-Crick geometry with both cytosine and thymine, as well as their analogs that have different carbohydrate moieties, or different nucleotides having the same hydrogen bonding patterns as cytidine and thymidine (e.g. uracil, pseudouridine, and 5-alkyl-uracil, all having the same hydrogen bonding patterns as thymine, or 5-hydroxymethyl- and 5-alkyl-cytosine, both having the same hydrogen as cytosine). These compounds are named "purine biversals".

DETAILED DESCRIPTION OF THE INVENTION

Figure 1:
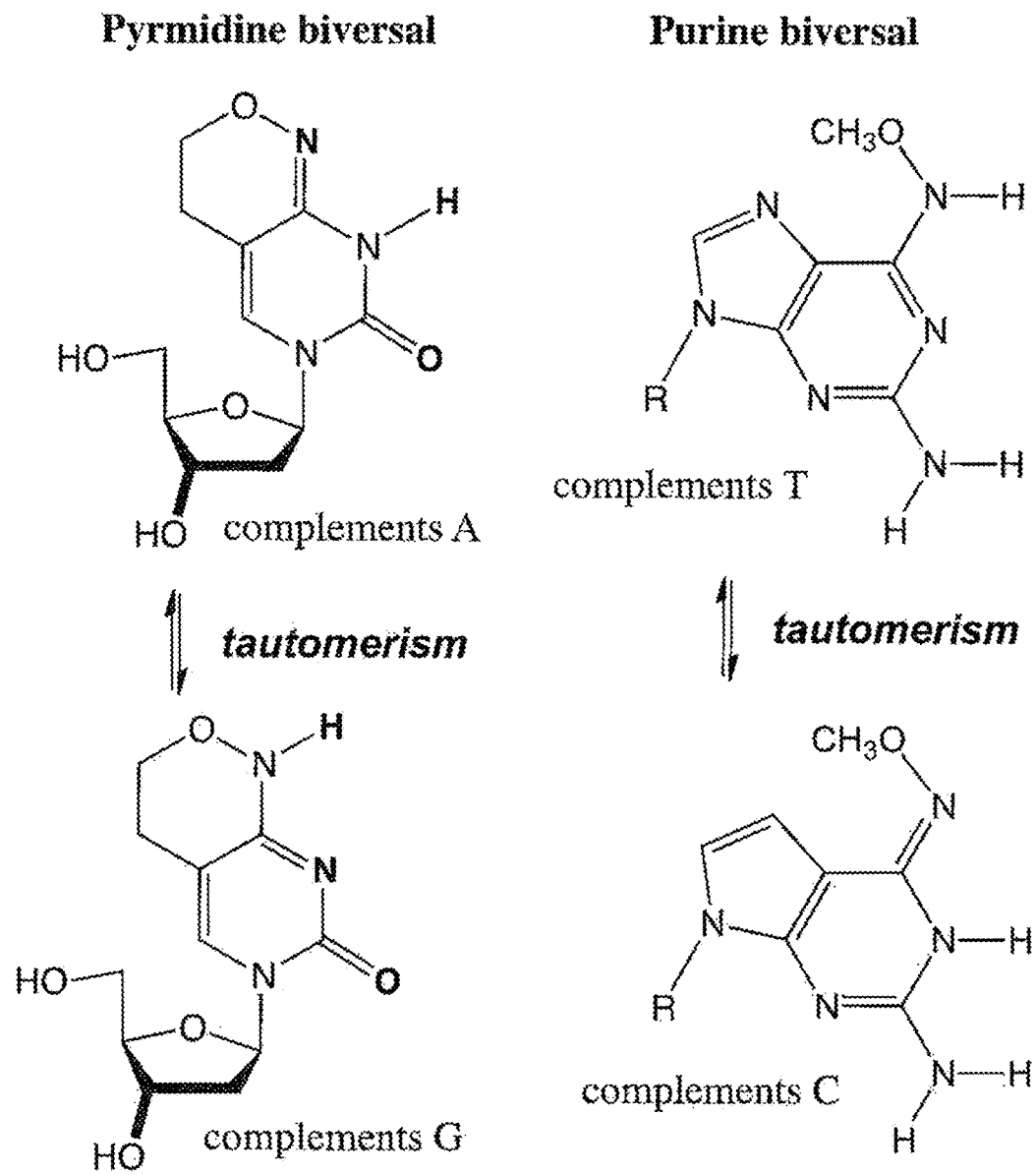
FIG. 1. The pyrimidine (left) [Lin, P. K., Brown, D. M. (1989) Synthesis and duplex stability of oligonucleotides containing cytosine-thymine analogues. *Nucl Acids Res.* 17, 10373-10383] and purine (right) biversals [Brown, D. M., Lin, P. K. T. (1991) Synthesis and duplex stability of oligonucleotides containing adenine-guanine analogs. *Carbohydrate Res.* 216, 129-139] presently known in the art.
Figure 2:
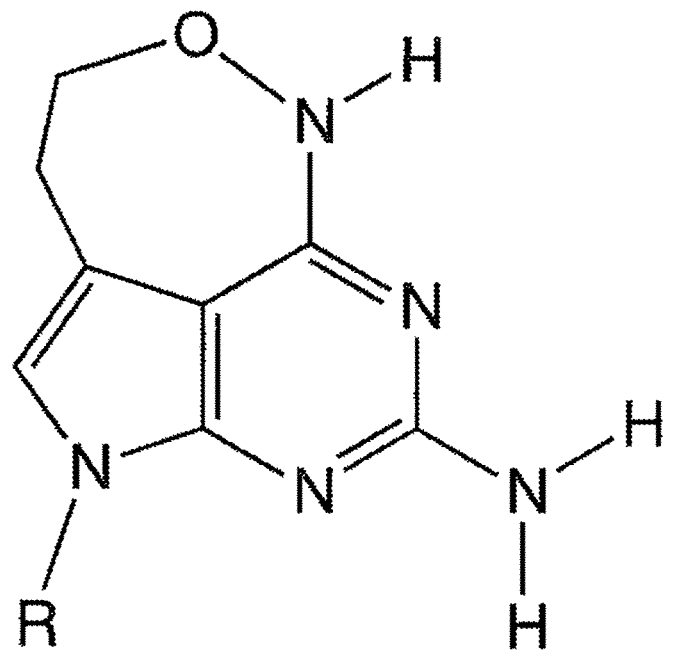
FIG. 2. The heterocycle of the instant invention, where are is the point of attachment of the heterocycle to a 2'-deoxyribose, a ribose, or the oligonucleotide of the instant invention.

The specific invention covers ribonucleosides, 2'-deoxyribonucleosides, and sugar analogues (for example threose, fluoro sugars, 2'-O-methoxy sugars, and others known in the art) that have the heterocycle shown in FIG. 2 attached to the carbohydrate, instead of a standard heterocycle. This system has two tautomeric forms, one with hydrogen atoms placed so it is complementary in the Watson-Crick sense to thymine and its analogs, and the other that is complementary to cytosine and its analogs.

In addition, this invention concerns oligonucleotides that contain this heterocyclic system, either embedded within the oligonucleotide chain, or at the 5'-end of the oligonucleotide (where its 5'-hydroxyl group can be free, or esterified with a monophosphate, diphosphate, or triphosphate group), or an oligonucleotide synthesized by solid phase phosphoramidites chemistry following procedures well-known in the art using phosphoramidites described in Example 1. Likewise, this invention covers processes that exploit these purine biversals as monophosphates, diphosphates, and triphosphates for enzymatic reactions, and processes that exploit oligonucleotides containing them, without limitation, in products and processes for binding to substantially complementary oligonucleotides, including those from natural sources, and especially where the precise sequence of the complementary oligonucleotide being detected is not known precisely.

Further, the invention includes compositions of matter that are building blocks for oligonucleotides that contain these purine biversals, The presently preferred implementation are the structures shown in the Figures, prepared as described in Example 1. As I well known in the art, functionally equivalent species can be obtained by derivatization in the minor groove. The procedure in Example 1 can be modified by methods well known in the art to make the corresponding D-ribonucleoside, as well as the enantiomeric species.

Example 1

The synthesis of a purine biversal as a 2'-deoxyribonucleoside is described.

Figure 3:
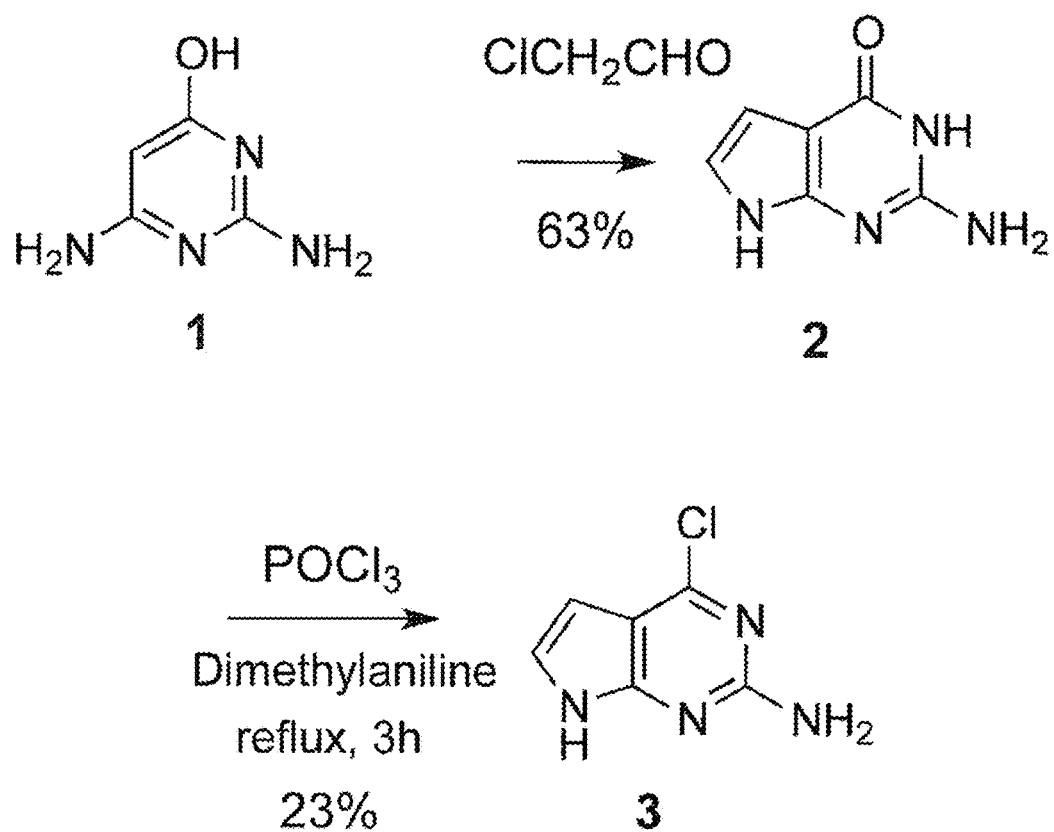
FIG. 3. Synthetic route for creating the heterocycle to be attached to the carbohydrate. Attaching a side chain to the heterocycle-2'-deoxyriboside.

Step 1. Creation of the heterocycle (FIG. 3). To a solution of 2,4-diamino-6-hydroxypyrimidine (1, 25.2 g) in DMF (480 mL) and water (80 mL) was added sodium acetate (27.2 g). The resulting yellow solution was stirred for 1 h. To the solution was added chloroacetaldehyde (50% solution, 25.4 mL) and the mixture was stirred at rt for 2 days. The volatiles were removed in vacuo and the residue was mixed with methanol (~70 mL) and stored at rt overnight. The resulting solid was filtered. The solid was mixed with methanol (150 mL) and heated at 60° C. for 10 min and cooled to rt overnight. The resulting solid was filtered and dried. The yield of 2 was 15 g to 19 g.

A mixture of 7-deazaguanine (14.2 g) and dimethylaniline (6 mL) in POCl$_3$ (200 mL) was refluxed for 3 h (bath temp. 130° C.). After cooling to rt, volatiles were removed by distillation (bath temp 60° C.). The residue was mixed with water (2~300 mL) and neutralized with ammonium hydroxide until complete precipitation of solid (pH~4). The resulting precipitate was filtered and further purified by column chromatography (silica, MC:MeOH=10:1) to give 3.6 g (21.4 mmol, 23%) of solid (FIG. 3).

Figure 4:
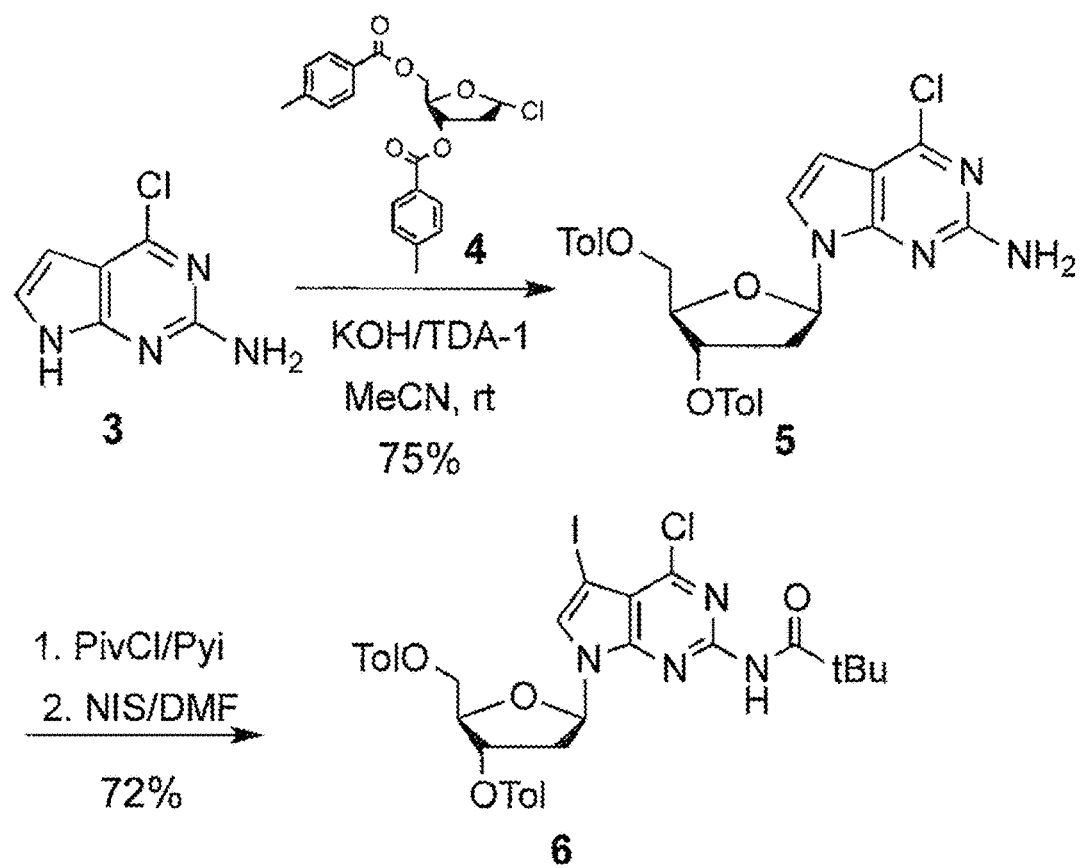
FIG. 4. Synthetic route for attaching the heterocycle to a carbohydrate derivative, and adding and iodine to it to prepare for the addition of a sidechain.

Step 2. Creating the nucleoside analog in preparation for addition of a side chain (FIG. 4). To a mixture of powdered KOH (2.6 g) in acetonitrile (150 mL) was added TDA-1 (0.27 mL) and the mixture was stirred for 5 min. To this mixture was added the amino chloro 7-deazapurine (3, 3.6 g) and the mixture was stirred for 5 min; the chloro-sugar (4, 9.1 g) was then added to the mixture. Stirring was continued for another 40 min (reaction complete by TLC). The mixture was adsorbed on silica gel and eluted with MC/EA until all the product was eluted. The filtrate was evaporated with silica gel and purified on silica column (MC:EA=20:1 to 10:1) to give a white solid (9.0 g, 17.3 mmol, 80%) which contains small amount of impurities. It was used for the next reaction without further purification (The actual yield could be around 75%)

A mixture of the starting material (9.6 g) and pivaloyl chloride (11.5 mL) in pyridine (95 mL) was stirred at rt for 2 h. TLC showed reaction was complete (Almost one spot, which is higher than starting material). Volatiles were removed by rotary evaporation and the residue was dissolved in dichloromethane/aq. HCl and extracted with dichloromethane. The organic layer was dried and purified on silica column to give a white solid (solvent is not easily removed by evaporation). It was dissolved in DMF (150 mL) and treated with N-iodosuccinimide (NIS, 6.2 g) and stirred at rt overnight. The mixture was mixed with water and extracted with dichloromethane. The organic layer (contained some DMF) was evaporated and purified on silica column.

Rf=0.3 (MC:Hx:EA=1:1:0.2) After column chromatography, the appropriate fractions were combined and evaporated to give white solid. It was treated with ethyl acetate/hexane and the resulting solid was filtered and dried. The filtrate was evaporated and stored at rt overnight. This was treated with ethyl acetate/hexane and the resulting solid was filtered. The filtered solids were combined. The filtrate was analyzed by TLC to confirm the existence of the product. The total yield was around 9.7 g, 13.3 mmol, 72%.

Figure 5:
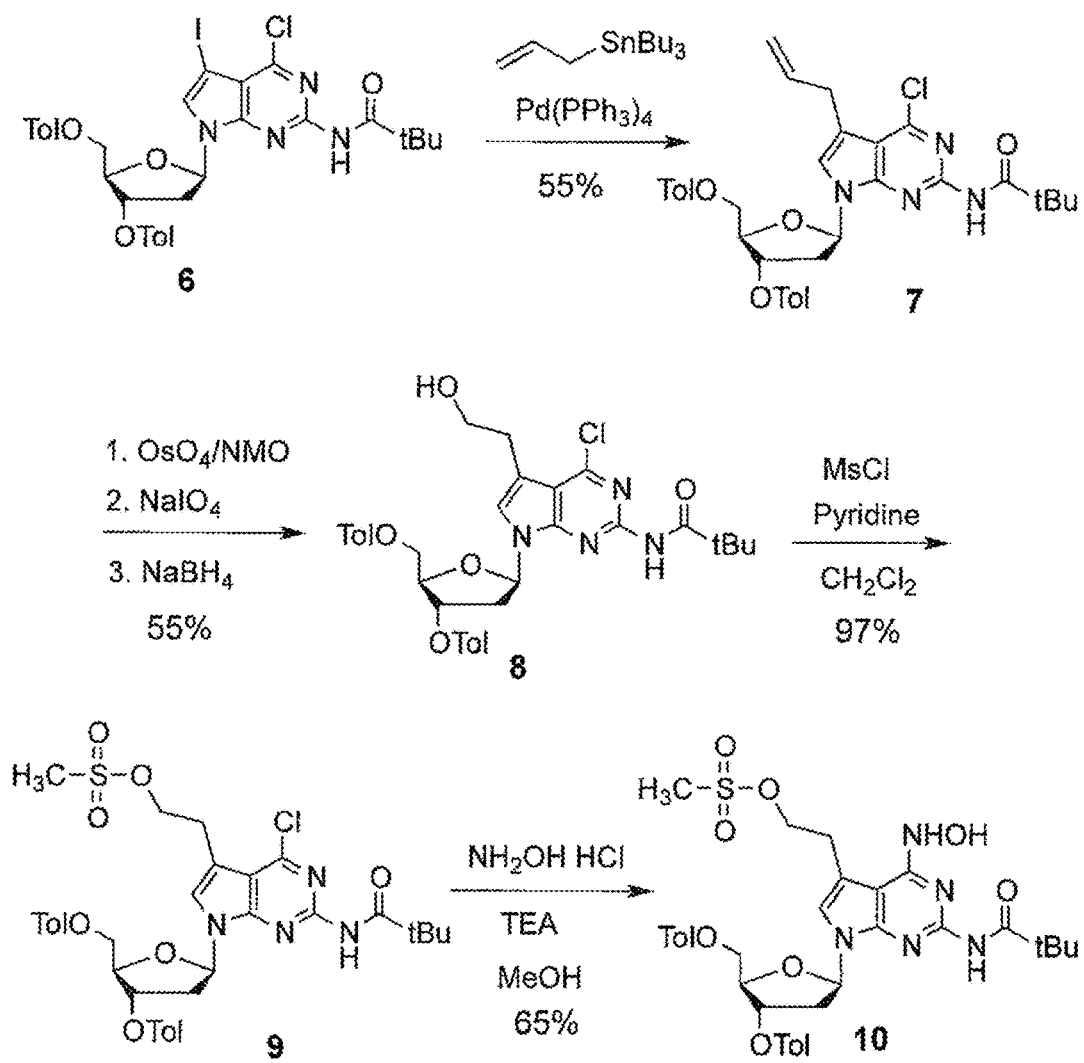
FIG. 5. Synthetic route for addition of a sidechain and preparation of the sidechain for the formation of the tricyclic heterocycle-2'-deoxyriboside.

Step 3. Forming a tagged heterocycle and its manipulation (FIG. 5). To a mixture of the starting material (6, 15.8 g) and Pd(PPh$_3$)$_4$ (4.7 g) in toluene (300 mL) was added allyl tributylstannane (16.2 mL) and the mixture was heated at 95° C. for 18 hours. After cooling to rt, the volatiles were removed by rotary evaporation and the residue was purified on silica column (MC to MC:EA) to give ~7.7 g of white solid (7, 11.9 mmol, 55%).

To a mixture of starting material (7, 7.7 g) and NMO (1.68 g, 1.2 eq) in acetone (390 mL) and water (65 mL) was added osmium tetroxide (4% in water, 1.5 mL, 0.02 eq) and the mixture was stirred at rt for 24 hours. The mixture was mixed with water and extracted with dichloromethane. Purification on silica column (Hx:EA=1:1 to EA 100%) gave white solid. It was dissolved in THF/H$_2$O (300 mL/150 mL) and treated with sodium periodate. Stirring was continued for 30 min and mixed with water and extracted with dichloromethane. Purification on silica column (MC:Hx=1:1 to MC:Hx:EA=3:3:2) gave an intermediate as a white solid. This white solid was dissolved in MeOH/THF (150 mL: 150 mL) then treated with sodium borohydride. The mixture was stirred at rt for 20 min (reaction complete). The mixture was mixed with water and extracted with dichloromethane to give 8. Purification of 8 on silica column (MC:Hx:EA=1:1:2) gave 4.3 g (6.6 mmol, 55% for 3 steps from the allyl compound) of white solid. Mp; 163~164° C.

This compound was then mesylated (FIG. 5). To a solution of starting material (8, 4.3 g) in dichloromethane (~100 mL) and pyridine (7 mL) was added methanesulfonyl chloride (3.5 mL). The mixture was stirred at rt for 2 hours. The mixture was washed with diluted HCl and purified on silica column, EA:Hx=1:2 to 1:1 (Rf=0.5, EA:Hx=1:1) to give a white solid. 4.7 g, 6.46 mmol, 97%. Mp; 66~67° C.

This was then prepared for cyclization. A mixture of starting material (9, 4.0 g, 5.5 mmol), hydroxylamine hydrochloride (3.82 g, 55 mmol) and trimethylamine (18 mL) in methanol (180 mL) and dioxane (180 mL) was stirred at 45° C. for 24 hrs. The mixture was mixed with water and organic solvents were removed by rotary evaporation. The mixture was extracted with ethyl acetate. The organic layer was evaporated and purified on silica column, EA:Hx=1:1 to give a white solid. 2.6 g, 3.6 mmol, 65%, mp; 82-83° C.

Figure 6:
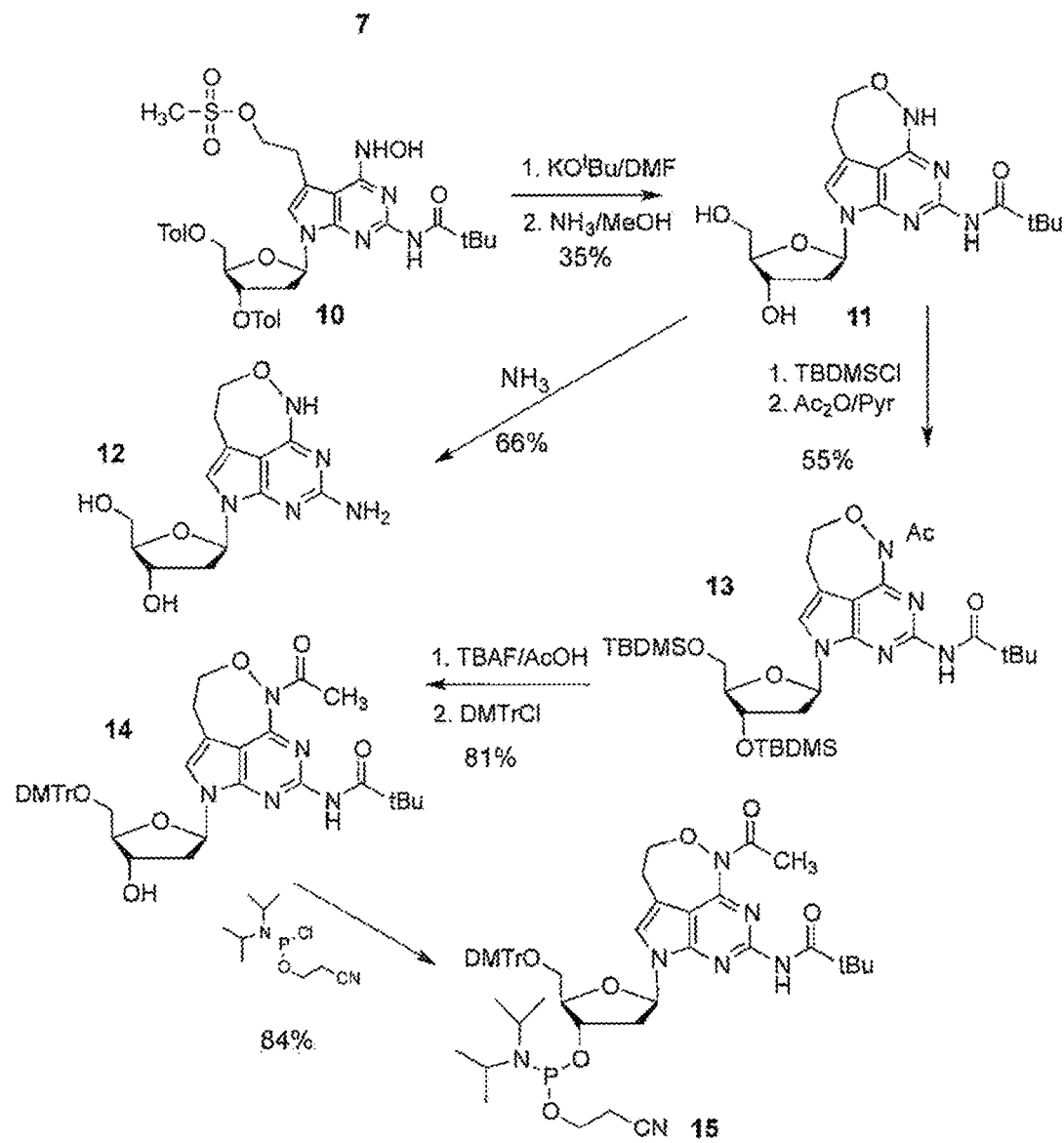
FIG. 6. Synthetic route for the formation of the tricyclic heterocycle-2'-deoxyriboside and its transformation to give protected phosphoramidites suitable for incorporation into oligonucleotides using solid phase synthesis.
Figure 7:
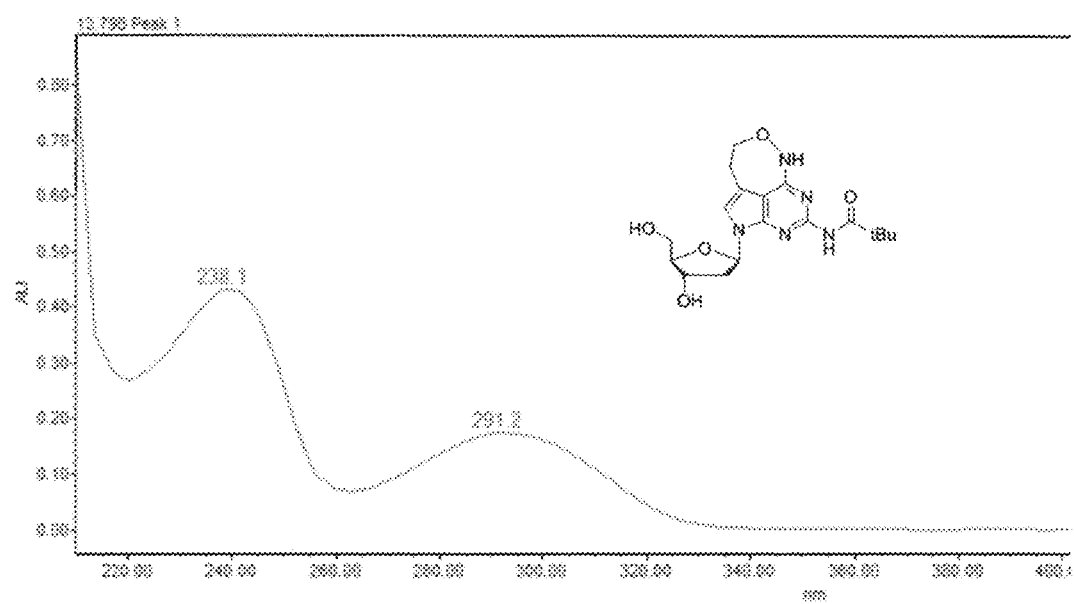
FIG. 7. UV spectrum of protected species, with a $\lambda_{max}$=291 nm
Figure 8:
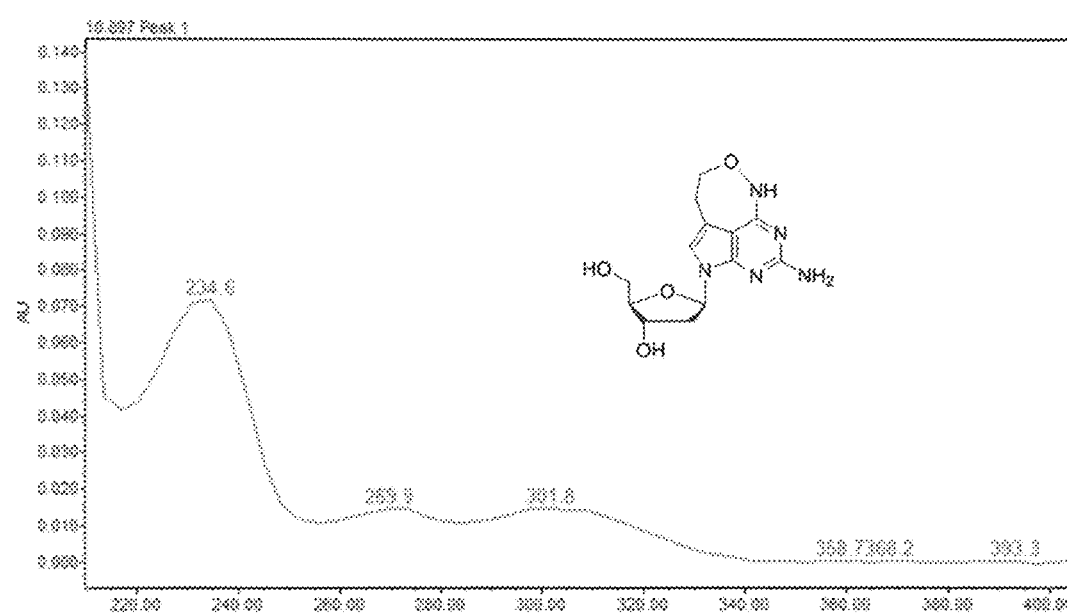
FIG. 8. UV spectrum of unprotected species; $\lambda_{max}$=301 nm ($\varepsilon$=5,050), 270 nm ($\varepsilon$=4,950), 237 nm ($\varepsilon$=23,700).
Figure 9:
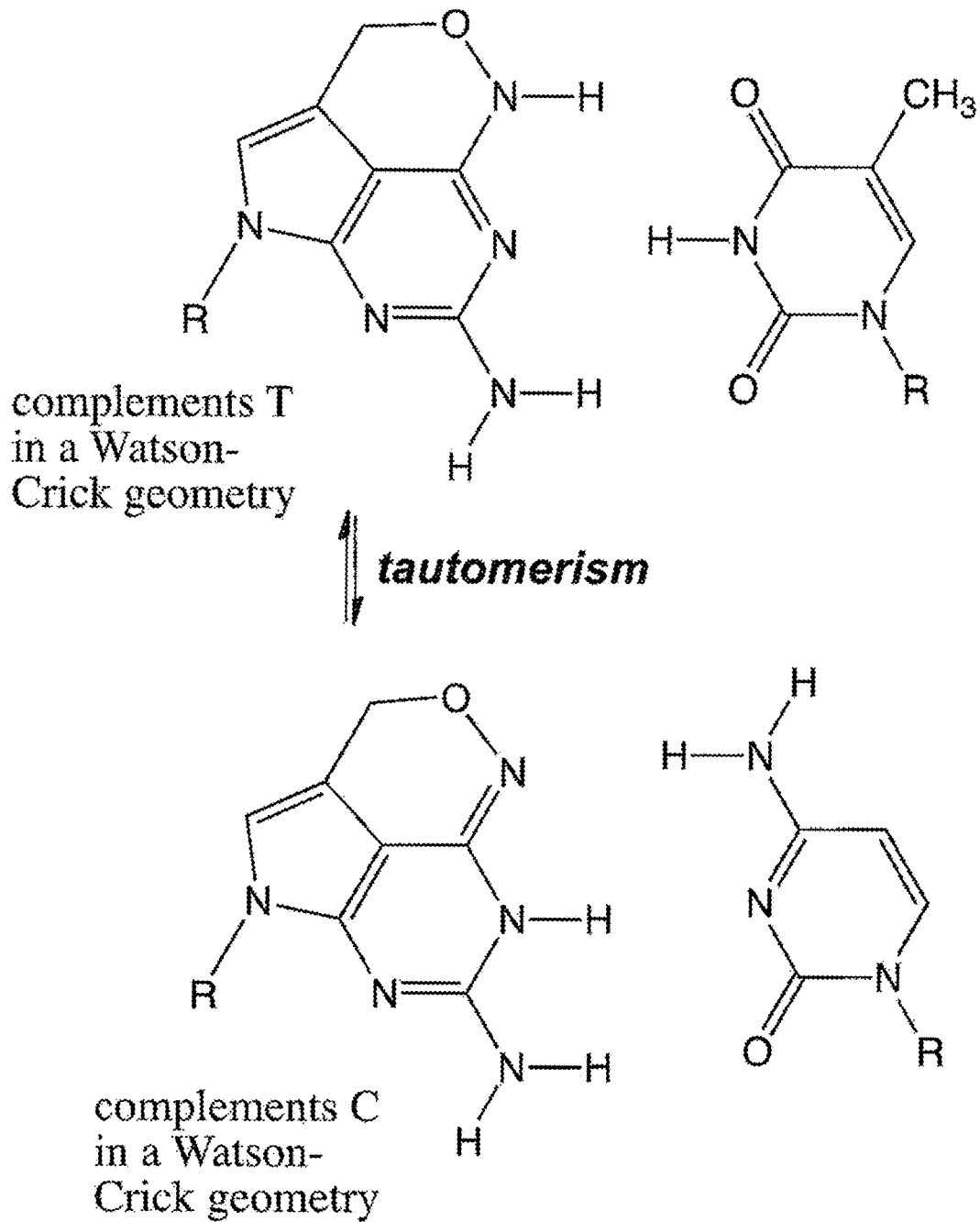
FIG. 9. Two tautomeric forms and their proposed pairs. R is the point of attachment to the carbohydrate in the DNA or RNA oligonucleotide.

Step 4. Cyclization and conversion to deprotected nucleoside and phosphoramidite suitable for solid phase DNA synthesis (FIG. 6). To a solution of starting material (2.6 g, 3.6 mmol) in DMF (~150 mL) was added potassium tert-butoxide (605 mg, 5.4 mmol). The mixture was stirred at rt for 8 hours. The mixture was mixed with water and extracted with ethyl acetate. The organic layer was evaporated and purified on silica column, MC:EA=5:1 to give a white solid (1.3 g, 2.1 mmol, 58%). This material could not be obtained pure form and contained some impurities. It was dissolved in saturated ammonia in methanol (50 mL) and stirred at rt for 24 hours. Volatiles were removed by rotary evaporation and the residue was purified on silica column, EA to EA:MeOH=10:1 to give a white solid, mp; 58~59° C., 490 mg, 1.25 mmol, 35%

For deprotection of the heterocycle (FIG. 6), a solution of the starting material (11, 25 mg) in methanol (0.2 mL) was mixed with ammonium hydroxide (2 mL) and the mixture was heated at 55° C. overnight. Volatiles were removed by rotary evaporation and the residue was purified on silica column (EA to EA:MeOH=8:1) to give a white solid, mp; 113~115° C., 13 mg, 0.042 mmol, 66%.

For preparation of the phosphoramidite, to a mixture of the starting material (500 mg, 1.28 mmol) and imidazole (436 mg, 6.4 mmol) in dichloromethane (15 mL) was added TBDMSCl (578 mg, 3.83 mmol) and the mixture was stirred at rt for 6 hrs. (Extended reaction gave tri-TBDMS product) It was mixed with water and extracted with dichloromethane. The organic layer was dried and evaporated, purified on silica column gave di-TBDMS product. This was dissolved in dichloromethane (15 mL) and pyridine (0.6 mL) and treated with acetic anhydride (0.4 mL). The mixture was stirred at rt for 30 min. It was mixed with diluted HCl and extracted with dichloromethane. The organic layer was dried and evaporated, purified on silica column, EA:Hx=1:1 to give a white solid, mp; 92~93° C., 466 mg, 0.70 mmol, 55%.

A mixture of the starting material (420 mg, 0.634 mmol), TBAF (2.5 mL, 1M in THF) and acetic acid (0.25 mL) in THF (20 mL) was stirred at 55° C. for 6 hours. The mixture was mixed with water and THF was removed by rotary evaporation. The residue was extracted with dichloromethane and purified on silica column, EA:MeOH=10:1 to give a white solid. It was dissolved in dichloromethane (10 mL) and 4-methylmorpholine (0.2 mL) and treated with dimethoxytrityl chloride (230 mg). The mixture was stirred at rt for 20 min and poured into water and extracted with dichloromethane. The organic layer was dried and evaporated, purified on silica column, EA:Hx=2:1 to EA 100% to give a white solid, mp; 110~12° C., 380 mg, 0.516 mmol, 81%.

Finally, to a mixture of the starting material (14, 365 mg, 0.496 mmol) and 4-methylmorpholine (0.2 mL) was added 2-cyanoethyl N,N-diisopropylchlorophosphoramidite (0.2 mL). The mixture was stirred at rt for 30 min and poured into water and extracted with dichloromethane. The organic layer was dried and evaporated, purified on neutral silica column, EA:Hx=1:1 to 2:1 to give a white solid (15) mp; 73~74° C., 390 mg, 0.416 mmol, 84%.

Developing Deprotection Conditions for the Biversal Purine Base in Oligonucleotides Synthesized by Solid Phase Phosphoramidite-Based Synthesis.

To a solution (20 □L) of protected nucleotide methanol was added ammonia solution (400 □L) or potassium carbonate (0.05 M in methanol, 69 mg/10 mL, 400 □L). The mixture was incubated in various conditions. Small portion (20 □L) of the mixture was diluted with 25 mM TEAA (180 □L) and analyzed by rp HPLC. The results are shown below.

1. Ammonia solution at room temperature

| | | | | Result (HPLC peak integration) | |
|---|---|---|---|---|---|
| | base | Temperature | Time | Deprotected (11.7 min) | Protected (14.6 min) |
| 1 | NH$_4$OH | rt | 1 day | 468 | 292 |
| 2 | NH$_4$OH | rt | 3 days | 725 | 111 |

Deprotection with ammonia solution at room temperature proceeded very slowly. Even after 3 days~15% of starting material was left unchanged.

2. Ammonia solution at 55° C.

| | | | | Result (HPLC peak integration) | |
|---|---|---|---|---|---|
| | base | Temperature | Time | Deprotected (11.7 min) | Protected (14.6 min) |
| 3 | NH$_4$OH | 55° C. | 1 h | 323 | 356 |
| 4 | NH$_4$OH | 55° C. | 2 h | 462 | 221 |
| 5 | NH$_4$OH | 55° C. | 4 h | 643 | 94 |
| 6 | NH$_4$OH | 55° C. | 6 h | 545 | 43 |
| 7 | NH$_4$OH | 55° C. | 22 h | 439 | 0 |

Deprotection with ammonia solution at 55° C. proceeded much faster than the deprotection at room temperature. After 6 hours, ~10% of starting material was left and the reaction was complete with overnight incubation. However, the amount of deprotected compound decreased with longer incubation without any noticeable side products. This implies the biversal purine decompose with long incubation in ammonia solution, but the decomposed products are not detectable by UV detection.

3. Potassium carbonate in methanol solution at 55° C.

| | | | | Result (HPLC peak integration) | |
|---|---|---|---|---|---|
| | base | Temperature | Time | Deprotected (11.7 min) | Protected (14.6 min) |
| 8 | K$_2$CO$_3$ | 55° C. | 1 h | 716 | 166 |
| 9 | K$_2$CO$_3$ | 55° C. | 2 h | 981 | 46 |
| 10 | K$_2$CO$_3$ | 55° C. | 4 h | 1052 | 0 |
| 11 | K$_2$CO$_3$ | 55° C. | 6 h | 1100 | 0 |
| 12 | K$_2$CO$_3$ | 55° C. | 18 h | 913 | 0 |

In 0.05 M potassium carbonate in methanol, the complete deprotection occurred in less than 4 hours. But, overnight incubation resulted decreased amount of deprotected compound. The optimum condition is 4~6 hours at 55° C.

Ammonia treatment of the protected biversal purine nucleoside was slow (at room temperature) or decomposed (at 55° C.). However, the deprotection with potassium carbonate in methanol was complete in 4 hours and did not show decomposition. These conditions are applied to oligomer containing biversal purine.

Stability of Duplexes Containing the Purine Biversal Base, Compared with the 6(N)Methoxydiamino Purine of Brown [Op. Cit.].

$T_m$ was measured with a solution containing each oligo (1.0 □M), NaCl (100 mM) and pH 7 buffer (20 mM sodium cacodylate). The heating and cooling cycle was run from 20° C. to 85° C. with 0.5° C./min gradient.

Results;

| | Sequence | Base pair X:Y | Tm | Base pair X:Y | Tm |
|---|---|---|---|---|---|
| 2B-Int | 5'-GAG TCT CGA CAX AGX TCC CAG AGG SEQ ID NO 1 3'-CTC AGA GCT GTY TCY AGG GTC TCC SEQ ID NO 2 | Biversal purine:C | 63 | F:C | 60 |
| | | Biversal purine:T | 68 | F:T | 62 |
| | | Biversal purine:G | 63 | F:G | 57 |
| | | Biversal purine:A | 59 | F:A | 58 |
| | | G:C | 72 | | |
| | | G:T | 60 | | |
| | | A:C | 55 | | |
| | | A:T | 67 | | |
| 2B-Ends | 5'-GAX TCT CGA CAG AGA TCC CAX AGG SEQ ID NO 3 3'-CTY AGA GCT GTC TCT AGG GTY TCC SEQ ID NO 4 | Biversal purine:C | 58 | F:C | 60 |
| | | Biversal purine:T | 65 | F:T | 61 |
| | | Biversal purine:G | 60 | F:G | 57 |
| | | Biversal purine:A | 59 | F:A | 57 |
| | | G:C | 69 | | |
| | | G:T | 57 | | |
| | | A:C | 56 | | |
| | | A:T | 64 | | |
| 3B | 5'-GAG TCT CGX CAG AGX TCC CAX AGG SEQ ID NO 5 3'-CTC AGA GCY GTC TCY AGG GTY TCC SEQ ID NO 6 | Biversal purine:C | 56 | F:C | 57 |
| | | Biversal purine:T | 65 | F:T | 59 |
| | | Biversal purine:G | 58 | F:G | 48 |
| | | Biversal purine:A | 54 | F:A | 53 |
| | | G:C | 71 | | |
| | | G:T | 55 | | |
| | | A:C | 51 | | |
| | | A:T | 67 | | |
| 4B | 5'-GAX TCT CGX CAG AGX TCC CAX AGG SEQ ID | Biversal purine:C | 46 | F:C | 52 |

-continued

| Sequence | Base pair X:Y | Tm | Base pair X:Y | Tm |
|---|---|---|---|---|
| NO 7 3'-CTY AGA GCY GTC TCY AGG GTY TCC SEQ ID NO 8 | Biversal purine:T | 64 | F:T | 54 |
| | Biversal Purine:G | No melting | F:G | 50 |
| | Biversal purine:A | 38? | F:A | 45 |
| | G:C | 72 | | |
| | G:T | 49 | | |
| | A:C | No melting | | |
| | A:T | 65 | | |

What is claimed is:

1. A compound having the structure

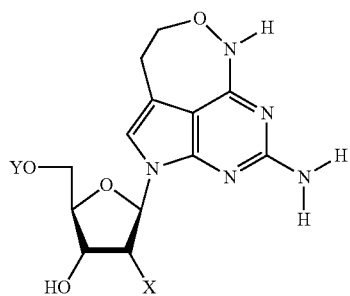

wherein X is either —H or —OH and Y is H, phosphate, diphosphates, or triphosphate.

2. The compound of claim 1, wherein X is —H.

3. An oligonucleotide chain that contains within it a nucleotide having the structure,

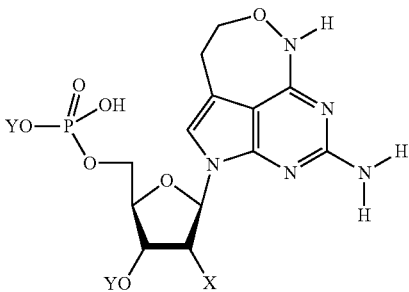

wherein X is either —H or —OH and Y is either H, phosphate, diphosphates, or the point of attachment of the remainder of the oligonucleotide chain to said nucleotide.

4. The oligonucleotide chain of claim 3, wherein X is —H.

5. A duplex between an oligonucleotide chain that contains within it a nucleotide unit having the structure

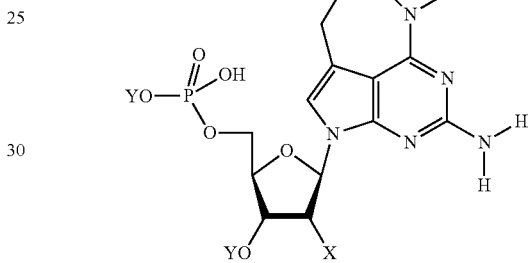

wherein X is either —H or —OH and Y is either H, phosphate, diphosphates, or the point of attachment of the remainder of the oligonucleotide chain to said nucleotide, and a substantially complementary oligonucleotide, wherein said duplex includes at least one Watson-Crick pair between said nucleotide unit in said oligonucleotide chain and a thymidine or a cytidine in said substantially complementary oligonucleotide.

* * * * *